(12) United States Patent
McKiernan et al.

(10) Patent No.: US 8,598,306 B2
(45) Date of Patent: Dec. 3, 2013

(54) MONOMER, POLYMER, AND METHOD OF MAKING IT

(75) Inventors: Mary McKiernan, Cottenham (GB); Jonathan Pillow, Baldock (GB)

(73) Assignees: Cambridge Display Technology Limited, Cambridgeshire (GB); Sumitomo Chemical Company Limited, Tokyo (JP)

( * ) Notice: Subject to any disclaimer, the term of this patent is extended or adjusted under 35 U.S.C. 154(b) by 87 days.

(21) Appl. No.: 13/258,550

(22) PCT Filed: Apr. 15, 2010

(86) PCT No.: PCT/GB2010/000800
§ 371 (c)(1),
(2), (4) Date: Nov. 28, 2011

(87) PCT Pub. No.: WO2010/119274
PCT Pub. Date: Oct. 21, 2010

(65) Prior Publication Data
US 2012/0095184 A1   Apr. 19, 2012

(30) Foreign Application Priority Data

Apr. 16, 2009 (GB) .................................. 0906544.2

(51) Int. Cl.
*C08G 63/02* (2006.01)

(52) U.S. Cl.
USPC ................ 528/397; 257/40; 313/504; 544/73

(58) Field of Classification Search
USPC ................ 257/40; 313/504; 544/73; 528/397
See application file for complete search history.

(56) References Cited

U.S. PATENT DOCUMENTS

| | | | |
|---|---|---|---|
| 5,150,006 | A | 9/1992 | Van Slyke et al. |
| 5,432,014 | A | 7/1995 | Sano et al. |
| 5,621,131 | A | 4/1997 | Kreuder et al. |
| 5,723,873 | A | 3/1998 | Yang |
| 5,798,170 | A | 8/1998 | Zhang et al. |
| 6,083,634 | A | 7/2000 | Shi |
| 6,268,695 | B1 | 7/2001 | Affinito |
| 6,353,083 | B1 | 3/2002 | Inbasekaran et al. |
| 7,030,138 | B2 | 4/2006 | Fujimoto et al. |
| 7,094,477 | B2 | 8/2006 | Kamatani et al. |
| 7,125,998 | B2 | 10/2006 | Stossel et al. |
| 7,147,935 | B2 | 12/2006 | Kamatani et al. |
| 7,238,435 | B2 | 7/2007 | Kamatani et al. |
| 2002/0117662 | A1 | 8/2002 | Nii |
| 2002/0182441 | A1 | 12/2002 | Lamansky et al. |
| 2008/0093987 | A1 | 4/2008 | Park et al. |

FOREIGN PATENT DOCUMENTS

| | | |
|---|---|---|
| EP | 0 707 020 A2 | 4/1996 |
| EP | 0 842 208 A1 | 5/1998 |
| EP | 0 880 303 A1 | 11/1998 |
| EP | 0 901 176 A2 | 3/1999 |
| EP | 0 947 123 A1 | 10/1999 |
| EP | 0 949 850 A1 | 10/1999 |
| EP | 1 245 659 | 10/2002 |
| GB | 2 348 316 A | 9/2000 |
| JP | 05-281766 A | 10/1993 |
| JP | 2002-324679 A | 11/2002 |
| KR | 10-2008-0079095 | 8/2008 |
| WO | WO-98/10621 A1 | 3/1998 |
| WO | WO-98/57381 A1 | 12/1998 |
| WO | WO-99/48160 A1 | 9/1999 |
| WO | WO-00/48258 A1 | 8/2000 |
| WO | WO-00/53656 A1 | 9/2000 |
| WO | WO-00/55927 A1 | 9/2000 |
| WO | WO-01/19142 A1 | 3/2001 |
| WO | WO-01/62869 A1 | 8/2001 |
| WO | WO-01/81649 A1 | 11/2001 |
| WO | WO-02/31896 A2 | 4/2002 |
| WO | WO-02/44189 A1 | 6/2002 |
| WO | WO-02/45466 A1 | 6/2002 |
| WO | WO-02/066552 A1 | 8/2002 |
| WO | WO-02/068435 A1 | 9/2002 |
| WO | WO-02/081448 A1 | 10/2002 |

(Continued)

OTHER PUBLICATIONS

Bernius et al., "Progress with Light-Emitting Polymers", *Adv. Mater.*, 12(23):1737-1750 (2000).

Chen et al., "Recent Developments in Molecular Organic Electroluminescent Materials," *Macromol. Sym.*, 125:1-48 (1997).

Kim et al., "PCPP Derivatives Containing Carbazole Pendant as Hole Transporting Moiety for Efficient Blue Electroluminescence," *Journal of Polymer Science, Part A: Polymer Chemistry*, 47(5):1327-1342 (2009).

Kim et al., "Syntheses and Characterization of Alkoxyphenyl-Substituted PCPP with Stabilized Blue Emission and Its Derivatives with Ketone Unit in the Main Chain," *Macromolecules*, 41:8324-8331 (2008).

Michaelson, "The work function of the elements and its periodicity", *J. Applied Physics*, 48(11): 4729-4733 (1977).

(Continued)

*Primary Examiner* — Terressa Boykin
(74) *Attorney, Agent, or Firm* — Marshall, Gerstein & Borun LLP

(57) ABSTRACT

A monomer having the general formula:

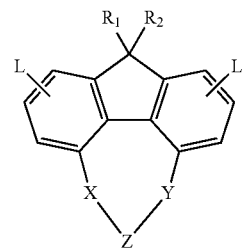

in which $R^1$ is any substitution; $R^2$ is any substitution; $R^1$ and $R^2$ may be linked to form a saturated or unsaturated ring; L represents a reactive leaving group; X and Y each independently represent $CR_2$, O, BR, NR, $SiR_2$, S, S=O, $SO_2$, PR or P=O(R) wherein R in each occurrence is independently selected from H or a substituent; Z represents a single bond or a divalent atom or group, wherein X—Z—Y forms an unconjugated ring or chain, with the proviso that at least one of $R^1$ and $R^2$ is an aryl or heteroaryl group if Z is a single bond.

19 Claims, 1 Drawing Sheet

(56) References Cited

FOREIGN PATENT DOCUMENTS

WO  WO-02/084759 A1  10/2002
WO  WO-03/018653 A1  3/2003
WO  WO-03/022908 A1  3/2003

OTHER PUBLICATIONS

Niu et al., "Thermal annealing below the glass transition temperature: A general way to increase performance of light-emitting diodes based on copolyfluorenes", *Applied Physics Letters*, 81(4):634-636 (2002).

Park et al., "A Blue-Light-Emitting Polymer with a Rigid Backbone for Enhanced Color Stability," *Adv. Funct. Mater.*, 17:3063-3068 (2007).

Setayesh et al., "Bridging the Gap between Polyfluorene and Ladder-Poly-*p*-phenylene: Synthesis and Charactrization of Poly-2,8-indenofluorene", *Macromolecules*, 33:2016-2020 (2000).

Song et al., "A Novel Conjugated Polymer Based on Cyclopenta[*def*]phenanthrene Backbone with Spiro Group," *Polymer*, 49:5643-5649 (2008).

Tokito et al., "Metal oxides as a hole-injecting layer for an organic electroluminescent device", *J. Phys. D: Appl. Phys.*, 29:2750-2753 (1996).

Yamaguchi et al., "Effects of B and C on the ordering of $L1_0$-CoPt thin films", *Applied Physics Letters*, 79(13):2001-2003 (2001).

Yamamoto, "Electrically Conducting and Thermally Stable π-Conjugated Poly (Arylene)s Prepared by Organometallic Processes", *Polymer Science*, 17:1153-1205 (1993).

Yang et al., "Efficient blue polymer light-emitting diodes from a series of soluble poly(paraphenylene)s", *J. Appl. Phys.*, 79(2):934-939 (1996).

Combined Search and Examination Report for Application No. GB0906544.2, dated Jul. 10, 2009.

Examination Report for Application No. GB0906544.2, dated Aug. 17, 2011.

International Preliminary Report on Patentability for Application No. PCT/GB2010/000800, dated Oct. 18, 2011.

International Search Report for Application No. PCT/GB2010/000800, dated Jul. 7, 2010.

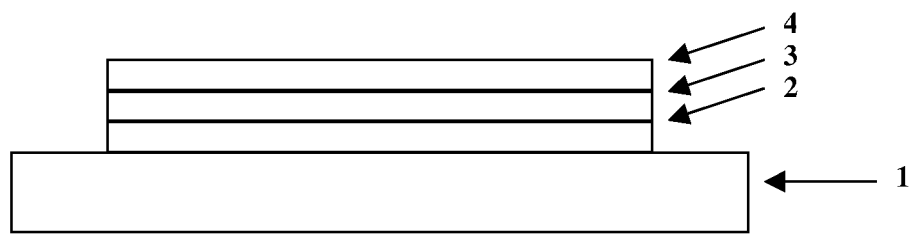

MONOMER, POLYMER, AND METHOD OF MAKING IT

FIELD OF THE INVENTION

The invention relates to compounds suitable for use as monomers, polymers comprising repeat units derived from said monomers, and methods for making the same. Such polymers are of particular use as semi-conductive polymers, particularly for use in electronic devices.

BACKGROUND OF THE INVENTION

Conjugated polymers are known to be utilized in varying electronic devices such as organic transistors, organic light emitting diodes (OLEDs) and organic photovotaic (PV) devices.

Polymer light emitting diodes (POLEDs) have been the subject of much interest and development over recent years, particularly in the field of display technology. The interest has been sparked owing to the many intrinsic advantages possessed by POLEDs over well-known liquid crystal display (LCD) devices. The significant advantage is the ability of the polymers to emit light, such that a separate light source is not required. This contrasts with the existing LCD devices in which an external light source has to be filtered in several stages in order to produce the final image. Thus, POLEDs also do not require any additional elements such as backlights and filters because they comprise polymer material which is manufactured on a transparent substrate of glass or plastic. POLEDs also have the benefit of being highly energy efficient, which makes them suitable candidates for low voltage operated ultra-thin lighting displays. POLEDs have the further benefit of being solution processable, enabling their formation by printing or solution casting techniques. One widely used class of polymers those comprising fluorene repeat units as disclosed in, for example, EP 0842208.

Presently known POLEDs can suffer from a limited lifetime, in particular as the polymers can be susceptible to a number of degradation pathways, comprising chemical, photochemical and electrochemical degradation. This can affect both the efficiency and the lifetime of the OLED. (By "lifetime" as used herein is meant the time taken for luminance to fall by 50% at constant current.) In the case of polyfluorenes, degradation may be the result of reactions at 4- and 5-positions of the fluorene unit.

Park et al, Adv. Funct. Mater, 2007, 17, 3063-3068 discloses poly(2,6-(4,4-bis(2-ethylhexyl)-8,9-dihydro-4H-cyclopenta-[def]-phenanthrene)) for the purpose of comparison with its dehydrogenated analogue poly(2,6-(4,4-bis(2-ethylhexyl)-4H-cyclopenta-[def]phenanthrene)), and comparison with polyfluorene. The authors suggest that this material is susceptible to easier degradation than the two materials it is compared with.

SUMMARY OF THE INVENTION

In a first aspect, the invention provides an optionally substituted compound.

In a first embodiment, the compound has the general formula:

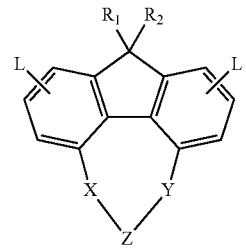

wherein
$R^1$ is any substitution;
$R^2$ is any substitution;
$R^1$ and $R^2$ may be linked to form a saturated or unsaturated ring;
L represents a reactive leaving group;
X and Y each independently represent $CR_2$, O, BR, NR, $SiR_2$, S, S=O, $SO_2$, PR or P=O(R), wherein R in each occurrence is independently selected from H or a substituent;
Z represents a single bond or a divalent atom or group, and
X—Z—Y forms an unconjugated ring or chain, with the proviso that at least one of $R^1$ and $R^2$ is an aryl or heteroaryl group if Z is a single bond.

Optionally, R, $R^1$ and $R^2$ are independently in each occurrence any one of a group consisting of optionally substituted straight, branched or cyclic alkyl wherein one or more non-adjacent C atoms may be replaced with O, S, NR, C=O and —COO—; or optionally substituted aryl or heteroaryl.

For the avoidance of doubt, "aryl" and "heteroaryl" as used herein include aromatic groups comprising more than one ring, in particular fused ring systems. One or more optional substituents may be present on these groups. Optional substituents for these aromatic groups include optionally substituted straight, branched or cyclic alkyl wherein one or more non-adjacent C atoms may be replaced with O, S, NR, C=O and —COO—, more preferably straight or branched alkyl.

Optionally, at least one of $R^1$ and $R^2$ is an alkyl group optionally substituted by one or more halogens, or an aryl or heteroaryl group having one or more optional substituents, each optional substituent being an alkyl group that may optionally be substituted by one or more halogens and in which one or more non-adjacent C atoms may be replaced with O, S, NR, C=O and —COO—.

Optionally, at least one of X and Y is —$CR_2$—.

Optionally, Z comprises a single bond or any one of the group consisting of —$(CR_2)_p$—, O, or NR; and wherein p is 1, 2, 3, 4, 5, or 6, and wherein —$(CR_2)_p$— may form a ring in the case where p is 4, 5 or 6.

Optionally, Z comprises a single bond or an alkylene group of the formula —$(CR_2)_p$—. In one preferred embodiment Z is a single bond. In another preferred embodiment, Z is —$CR_2$— (i.e. p=1)

Optionally, R in each occurrence is H or alkyl.

Optionally, each L is independently selected from the group consisting of boronic acid or ester thereof, chlorine, bromine or iodine. Preferably, each L is independently selected from bromine or boronic acid or an ester thereof.

Optionally, the compound has the following formula:

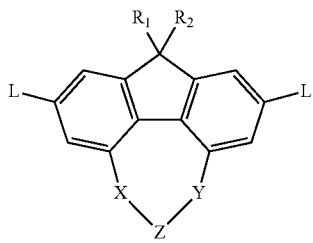

Conjugation with adjacent repeat units is maximised by providing the L groups in the shown position.

In a second aspect the invention provides a polymer as specified in claims 10 to 13.

In one embodiment the polymer comprises repeat units of formula:

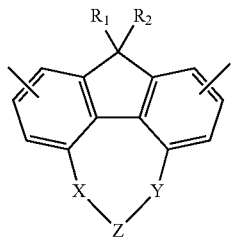

wherein $R^1$ and $R^2$, X, Y and Z are as described with respect to the first aspect of the invention.

Optionally, said polymer is a semi-conducting polymer.
Optionally, the polymer comprises arylene co-repeat units.
Optionally, said polymer is a light-emitting polymer.

In a third aspect, the invention provides a method of manufacturing a polymer according to the second aspect of the invention, comprising the step of polymerization of a compound according to the first aspect of the invention.

Optionally, said polymerization occurs in the presence of a metal catalyst.

Optionally, said metal catalyst is a palladium catalyst.

In a fourth aspect, the invention provides an electronic device comprising the polymer of the second aspect of the invention.

Optionally, said device is a light emitting diode, a field effect transistor or a photo-voltaic device.

Optionally, said device is a light emitting diode.

BRIEF DESCRIPTION OF THE DRAWINGS

For a better understanding of the invention and to show how the same may be carried into effect, reference will now be made by way of example only to the accompanying drawing, wherein:

FIG. 1 illustrates the architecture of an electroluminescent device according to the invention.

DETAILED DESCRIPTION OF THE INVENTION

The inclusion of the X—Z—Y group in accordance with the invention provides increased stability to polymers, in particular by blocking reactions at the 4- and 5-positions of the fluorene unit.

Exemplary compounds according to the invention have the following formulae:

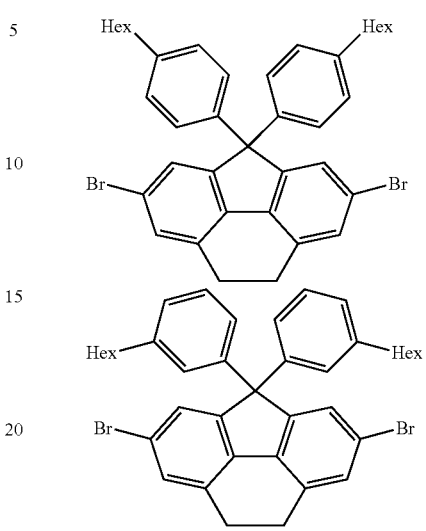

In the above examples, substituents $R^1$ and $R^2$ comprise substituted phenyl. This aromatic substituent has been found to increase stability of the repeat unit, and the presence of the alkyl group serves to increase solubility of the resultant polymer.

The following units illustrate alternative X—Z—Y groups, in which X—Z—Y forms a chain:

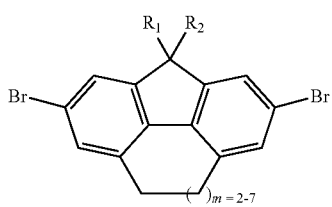

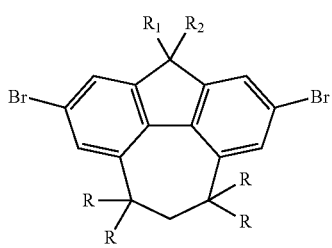

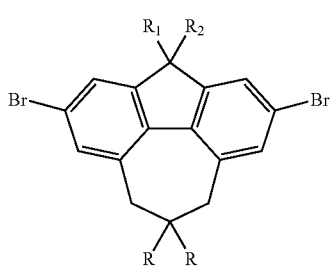

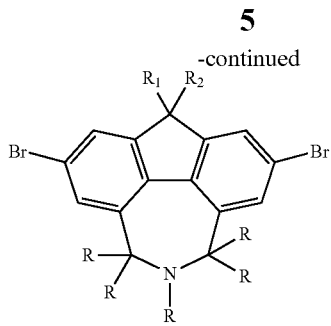

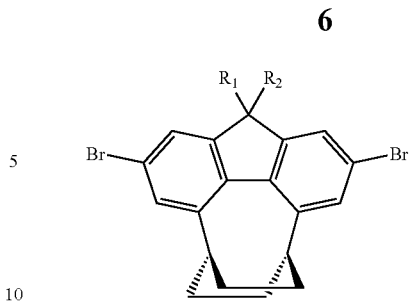

For simplicity, the compounds above are illustrated with bromine leaving groups however it will be appreciated that these groups may be replaced with any reactive leaving group.

The invention provides a more stabilized structure by the presence of the non-conjugated group on the opposite side of the fluorene molecule to the C9 carbon. Thus, the incorporation of the X—Y—Z form provides enhanced stability to the modified compound structure of the monomeric unit and hence of the polymer, particularly with respect to the chemical, photochemical or electrochemical degradation pathways that lead to reduced photoluminescence efficiency and limit the lifetime of OLEDs comprising polyfluorenes. Consequently, the problems associated with a decline in light emitting efficiency which are observed in polymers comprising this compound are diminished and a polymer exhibiting prolonged colour stability and minimized degradation is achieved.

Synthesis

Monomers according to the invention may be synthesized according to the following scheme:

Alternatively, X—Z—Y may form a ring structure, as shown below wherein X—Z—Y form a cyclohexyl group:

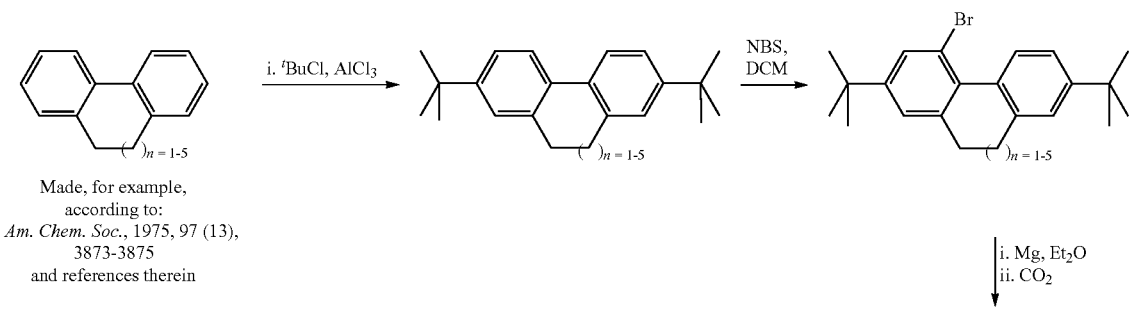

Made, for example, according to:
J. Am. Chem. Soc., 1975, 97 (13), 3873-3875
and references therein

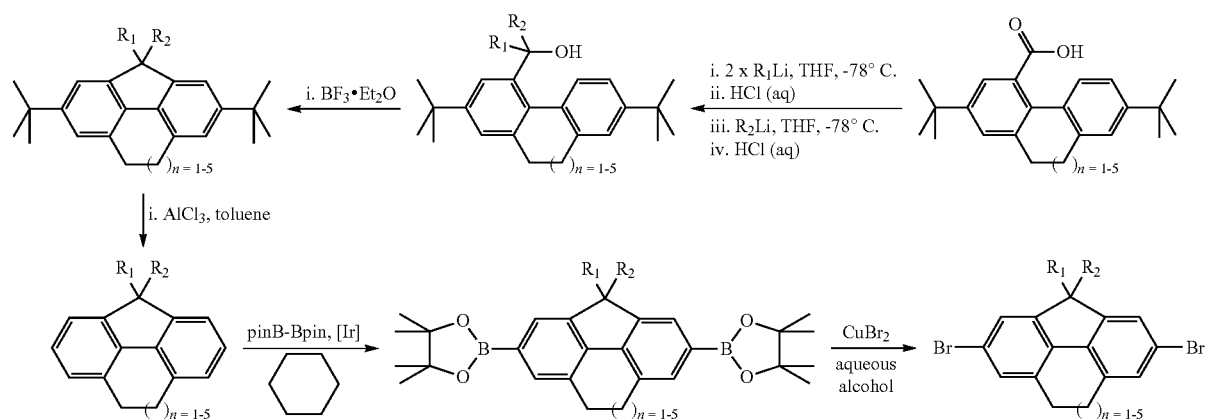

Co-Repeat Units

Polymers of the present invention comprise at least one of the repeat units described above, and preferably comprise one or more further repeat units. These further repeat units may be selected so as to tune the properties of the polymer of the invention according to its desired use, in particular its use as either a hole transporting, electron transporting and/or electroluminescent polymer.

Arylenes form one class of preferred further repeat units. Preferred arylene repeat units are selected from arylene repeat units as disclosed in, for example, Adv. Mater. 2000 12(23) 1737-1750 and references therein, in particular 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Fluorene repeat units of the following structure are particularly preferred:

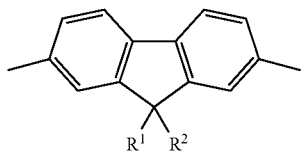

wherein $R^1$ and $R^2$ are as described above.

The polymer of the invention may comprise an arylamine repeat unit, optionally in combination with an arylene unit as described above. Preferred arylamine repeat units have the following formula:

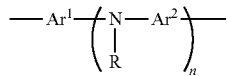

wherein $Ar^1$ and $Ar^2$ are optionally substituted aryl or heteroaryl groups, n is greater than or equal to 1, preferably 1 or 2, and R is H or a substituent, preferably a substituent. R is preferably alkyl or aryl or heteroaryl, most preferably aryl or heteroaryl. Any of the aryl or heteroaryl groups in the unit of formula 1 may be substituted. Preferred substituents include alkyl and alkoxy groups. Any of the aryl or heteroaryl groups in the repeat unit of Formula 1 may be linked by a direct bond or a divalent linking atom or group. Preferred divalent linking atoms and groups include O, S; substituted N; and substituted C.

Particularly preferred units satisfying Formula 1 include units of Formulae 1-3:

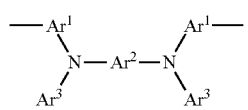

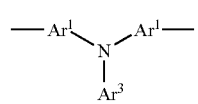

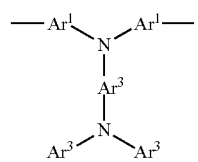

wherein $Ar^1$ and $Ar^2$ are as defined above; and $Ar^3$ is optionally substituted aryl or heteroaryl. Where present, preferred substituents for $Ar^3$ include alkyl and alkoxy groups.

Preferred concentration of the arylamine unit depends on the function of the polymer containing it. If the arylamine unit is present in a polymer for use in a hole transport layer it is preferably present in an amount up to 95 mol %, preferably up to 70 mol %. If the arylamine unit is present in a polymer for use in an emissive layer (as an emissive polymer or as the host for an emissive dopant) it is preferably present in an amount up to 30 mol %, preferably up to 20 mol %. These percentages apply to the total number of arylamine units present in the polymer in the case where more than one type of arylamine repeat unit is used.

The polymer may comprise heteroarylene repeat units for charge transport or emission. Preferred heteroarylene repeat units are selected from formulae 7-21:

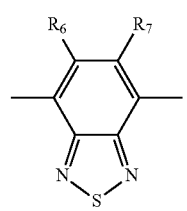

wherein $R_6$ and $R_7$ are the same or different and are each independently hydrogen or a substituent group, preferably alkyl, aryl, perfluoroalkyl, thioalkyl, cyano, alkoxy, heteroaryl, alkylaryl or arylalkyl. For ease of manufacture, $R_6$ and $R_7$ are preferably the same. More preferably, they are the same and are each a phenyl group.

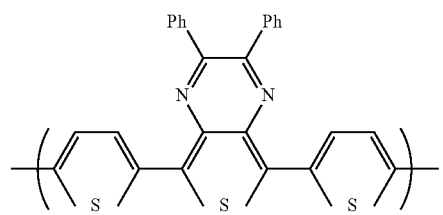

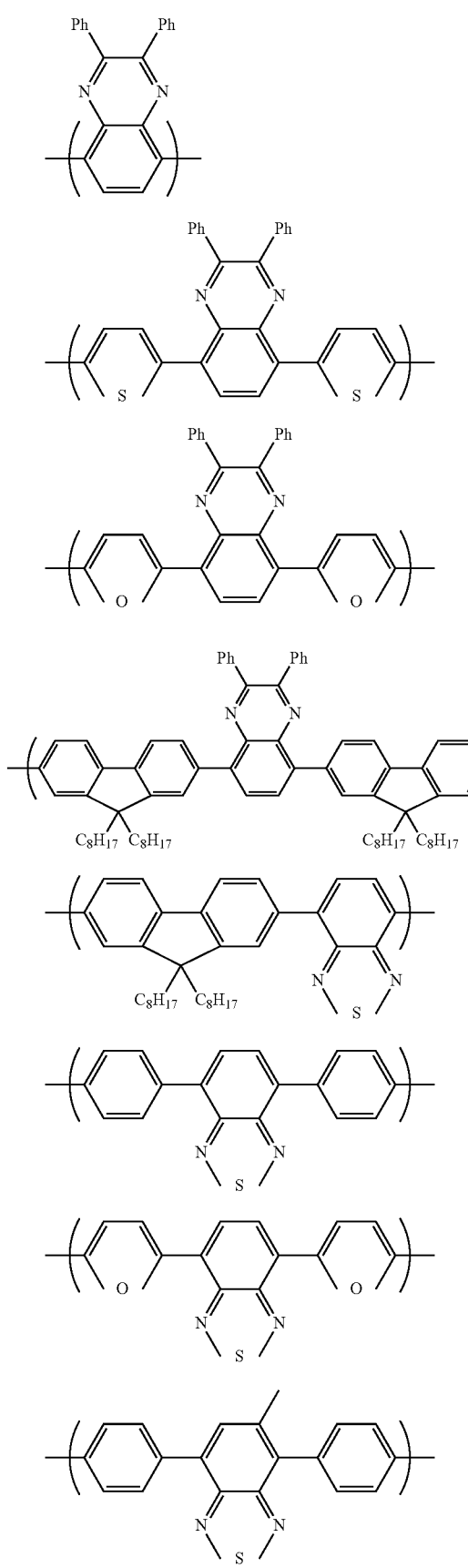
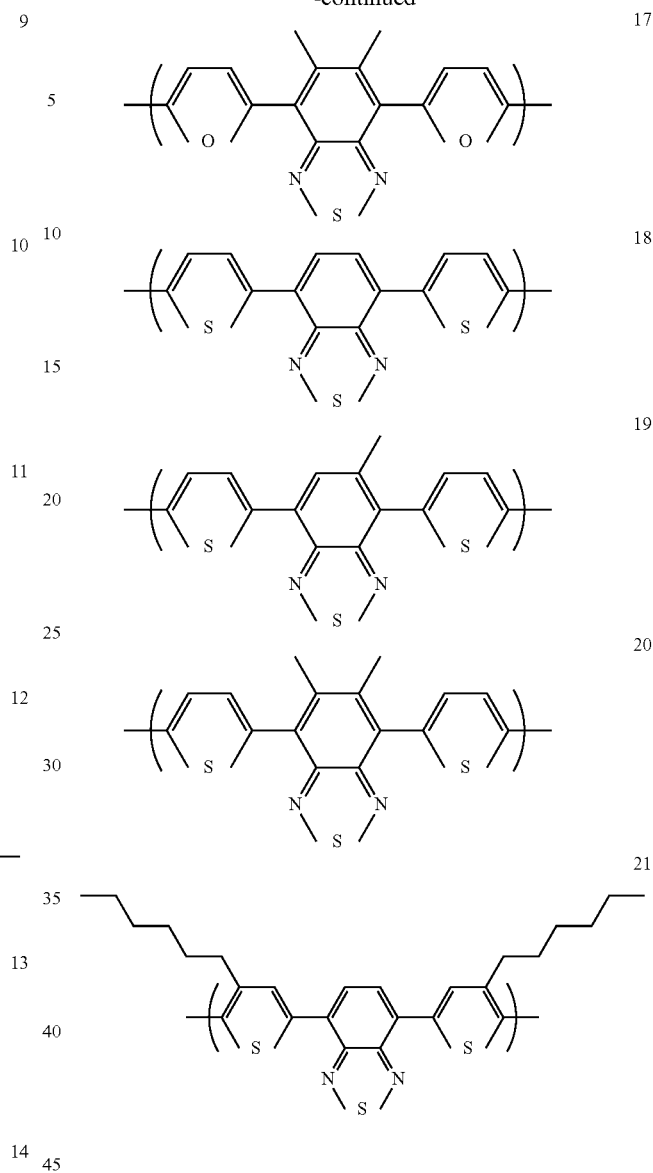

Electroluminescent copolymers may comprise an electroluminescent region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality. Alternatively, an electroluminescent polymer may be blended with a hole transporting material and/or an electron transporting material. Polymers comprising one or more of a hole transporting repeat unit, electron transporting repeat unit and emissive repeat unit may provide said units in a polymer main-chain or polymer side-chain.

The different regions within such a polymer may be provided along the polymer backbone, as per U.S. Pat. No. 6,353,083, or as groups pendant from the polymer backbone as per WO 01/62869.

Polymers may provide one or more of the functions of hole transport, electron transport and emission depending on which layer of the device it is used in and the nature of co-repeat units.

Polymerisation Methods

Preferred methods for preparation of these polymers are Suzuki polymerization as described in, for example, WO 00/53656 and Yamamoto polymerization as described in, for example, T. Yamamoto, "Electrically Conducting And Thermally Stable π-Conjugated Poly(arylene)s Prepared by Organometallic Processes", Progress in Polymer Science 1993, 17, 1153-1205. These polymerization techniques both operate via a "metal insertion" wherein the metal atom of a metal complex catalyst is inserted between an aryl group and a leaving group of a monomer. In the case of Yamamoto polymerization, a nickel complex catalyst is used; in the case of Suzuki polymerization, a palladium complex catalyst is used.

For example, in the synthesis of a linear polymer by Yamamoto polymerization, a monomer having two reactive halogen groups is used. Similarly, according to the method of Suzuki polymerization, at least one reactive group is a boron derivative group such as a boronic acid or boronic ester and the other reactive group is a halogen. Preferred halogens are chlorine, bromine and iodine, most preferably bromine.

It will therefore be appreciated that repeat units and end groups comprising aryl groups as illustrated throughout this application may be derived from a monomer carrying a suitable leaving group.

Suzuki polymerization may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

Solution Processing

A single polymer or a plurality of polymers may be deposited from solution to form the electroluminescent layer. Suitable solvents include mono- or poly-alkylbenzenes such as toluene and xylene. Particularly preferred solution deposition techniques are spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full color displays. A device may be inkjet printed by providing a patterned layer over the first electrode and defining wells for printing of one color (in the case of a monochrome device) or multiple colors (in the case of a multicolor, in particular full color device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

Polymers of the inventions may be used as hosts for fluorescent or phosphorescent dopants. In the case of a phosphorescent host, host material should have a $T_1$ energy level sufficiently high for excited state energy to be transferred from the $T_1$ energy level of the host to the T1 level of the emitter. Preferably, the host has a $T_1$ energy level sufficiently high to prevent energy back-transfer from the $T_1$ energy level of the emitter, and in particular a $T_1$ energy level higher than that of the emitter. However, in some cases the $T_1$ energy level of the host may be the same, or even lower, than that of the emitter.

Light-emitting dopants are preferably metal complexes. Preferred metal complexes comprise optionally substituted complexes of formula (V):

$$ML^1_q L^2_r L^3_s \quad (V)$$

wherein M is a metal; each of $L^1$, $L^2$ and $L^3$ is a coordinating group; q is an integer; r and s are each independently 0 or an integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, pallaidum, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission color is determined by the choice of the metal. The sharp emission is generally narrow, resulting in a pure color emission useful for display applications.

The d-block metals are particularly suitable for emission from triplet excited states. These metals form organometallic complexes with carbon or nitrogen donors such as porphyrin or bidentate ligands of formula (VI):

(VI)

wherein $Ar^4$ and $Ar^5$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

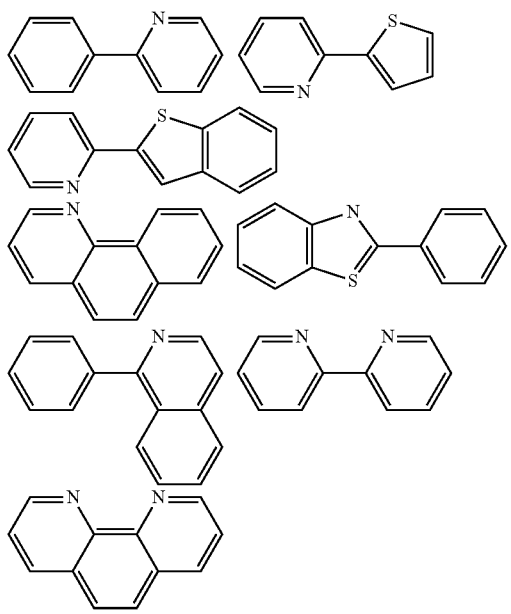

Each of Ar⁴ and Ar⁵ may carry one or more substituents. Two or more of these substituents may be linked to form a ring, for example an aromatic ring. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the core and dendritic branches comprises an aryl or heteroaryl group.

Other ligands suitable for use with d-block elements include diketonates, in particular acetylacetonate (acac); tri-arylphosphines and pyridine, each of which may be substituted.

Main group metal complexes show ligand based, or charge transfer emission. For these complexes, the emission color is determined by the choice of ligand as well as the metal.

The host material and metal complex may be combined in the form of a physical blend. Alternatively, the metal complex may be chemically bound to the host material. In the case of a polymeric host, the metal complex may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

A wide range of fluorescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014]. Suitable ligands for di or trivalent metals include: oxinoids, e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission color.

General Device Architecture

With reference to FIG. 1, the architecture of an electroluminescent device according to the invention comprises a transparent glass or plastic substrate 1, an anode 2 and a cathode 4. An electroluminescent layer 3 is provided between anode 2 and cathode 4. An electroluminescent device according to the invention will comprise a polymer of the invention as described above in electroluminescent layer 3 or in a charge transporting layer (now shown).

In a practical device, at least one of the electrodes is semi-transparent in order that light may be emitted. Where the anode is transparent, it typically comprises indium tin oxide.

Charge Transport Layers

Further layers may be located between anode 2 and cathode 3, such as charge transporting, charge injecting or charge blocking layers.

In particular, it is desirable to provide a conductive hole injection layer, which may be formed from a conductive organic or inorganic material provided between the anode 2 and the electroluminescent layer 3 to assist hole injection from the anode into the layer or layers of semiconducting polymer. Examples of doped organic hole injection materials include doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and poly(thienothiophene). Examples of conductive inorganic materials include transition metal oxides such as VOx MoOx and RuOx as disclosed in Journal of Physics D: Applied Physics (1996), 29(11), 2750-2753.

If present, a hole transporting layer located between anode 2 and electroluminescent layer 3 preferably has a HOMO level of less than or equal to 5.5 eV, more preferably around 4.8-5.5 eV. HOMO levels may be measured by cyclic voltammetry, for example.

If present, an electron transporting layer located between electroluminescent layer 3 and cathode 4 preferably has a LUMO level of around 3-3.5 eV.

Electroluminescent Layer

Electroluminescent layer 3 may consist of the electroluminescent material alone or may comprise the electroluminescent material in combination with one or more further materials. In particular, the electroluminescent material may be blended with hole and/or electron transporting materials as disclosed in, for example, WO 99/48160, or may comprise a luminescent dopant in a semiconducting host matrix. Alternatively, the electroluminescent material may be covalently bound to a charge transporting material and/or host material.

Electroluminescent layer 3 may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Cathode

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminum. Alternatively, it may comprise a plurality of metals, for example a bilayer of a low workfunction material and a high workfunction material such as calcium and aluminum as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode will comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum. Examples of transparent cathode devices are disclosed in, for example, GB 2348316.

Encapsulation

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to preventingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

The embodiment of FIG. 1 illustrates a device wherein the device is formed by firstly forming an anode on a substrate followed by deposition of an electroluminescent layer and a cathode, however it will be appreciated that the device of the invention could also be formed by firstly forming a cathode on a substrate followed by deposition of an electroluminescent layer and an anode.

The invention claimed is:

1. An optionally substituted compound having the general formula:

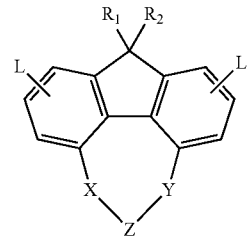

wherein
R$^1$ is any substitution; R$^2$ is any substitution; R$^1$ and R$^2$ may be linked to form a saturated or unsaturated ring;
L represents a reactive leaving group;
X and Y each independently represent CR$_2$, O, BR, NR, SiR$_2$, S, S=O, SO$_2$, PR or P=O(R) wherein R in each occurrence is independently selected from H or a substituent;
Z represents a single bond or a divalent atom or group,
wherein X—Z—Y forms an unconjugated ring or chain, and at least one of R$^1$ and R$^2$ is an aryl or heteroaryl group if Z is a single bond.

2. A compound according to claim 1, wherein R, R$^1$ and R$^2$ are independently in each occurrence any one of a group consisting of optionally substituted straight, branched or cyclic alkyl wherein one or more non-adjacent C atoms may be replaced with O, S, NR, C=O and —COO—; or optionally substituted aryl or heteroaryl.

3. A compound according to claim 2, wherein at least one of R$^1$ and R$^2$ is an alkyl group optionally substituted by one or more halogens, or an aryl or heteroaryl group having one or more optional substituents, each optional substituent being an alkyl group that may optionally be substituted by one or more halogens and in which one or more non-adjacent C atoms may be replaced with O, S, NR, C=O and —COO—.

4. A compound according to claim 1, wherein at least one of X and Y is —CR$_2$—.

5. A compound according to claim 1, wherein Z comprises a single bond or any one of the group consisting of —(CR$_2$)$_p$—, O, or NR; and wherein p is 1, 2, 3, 4, 5, or 6, and wherein —(CR$_2$)$_p$— may form a ring in the case where p is 4, 5 or 6.

6. A compound according to claim 1, wherein Z comprises a single bond or an alkylene group of the formula —(CR$_2$)$_p$—.

7. A compound according to claim 1 wherein R in each occurrence is H or alkyl.

8. A compound according to claim 1 wherein each L is independently selected from the group consisting of boronic acids, boronic esters, chlorine, bromine, and iodine.

9. A compound according to claim 1 of formula:

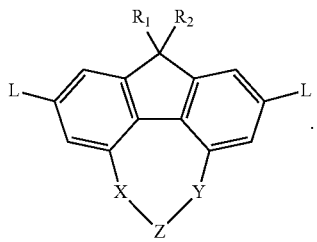

10. A polymer comprising repeat units of formula:

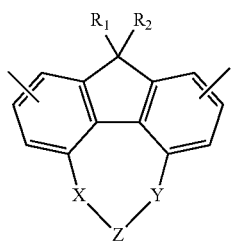

wherein $R^1$ and $R^2$, X, Y and Z are as defined as follows:
$R^1$ is any substitution; $R^2$ is any substitution; $R^1$ and $R^2$ may be linked to form a saturated or unsaturated ring;
X and Y each independently represent $CR_2$, O, BR, NR, $SiR_2$, S, S=O, $SO_2$, PR or P=O(R) wherein R in each occurrence is independently selected from H or a substituent;
Z represents a single bond or a divalent atom or group,
wherein X—Z—Y forms an unconjugated ring or chain, and at least one of $R^1$ and $R^2$ is an aryl or heteroaryl group if Z is a single bond.

11. A polymer according to claim 10, wherein said polymer is a semi-conducting polymer.

12. A polymer according to claim 10 wherein the polymer comprises arylene co-repeat units.

13. A polymer according to claim 10, wherein said polymer is a light-emitting polymer.

14. A method of manufacturing a polymer according to claim 10, comprising polymerizing of an optionally substituted compound having the general formula:

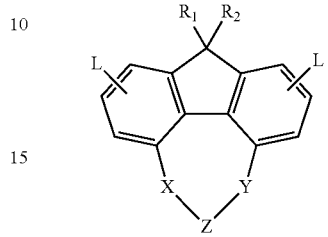

wherein
$R^1$ is any substitution; $R^2$ is any substitution; $R^1$ and $R^2$ may be linked to form a saturated or unsaturated ring;
L represents a reactive leaving group;
X and Y each independently represent $CR_2$, O, BR, NR, $SiR_2$, S, S=O, $SO_2$, PR or P=O(R) wherein R in each occurrence is independently selected from H or a substituent;
Z represents a single bond or a divalent atom or group,
wherein X—Z—Y forms an unconjugated ring or chain, and at least one of $R^1$ and $R^2$ is an aryl or heteroaryl group if Z is a single bond.

15. A method according to claim 14, wherein said polymerizing occurs in the presence of a metal catalyst.

16. A method according to claim 15, wherein said metal catalyst is a palladium catalyst.

17. An electronic device comprising the polymer of claim 1.

18. An electronic device according to claim 17, wherein said device is a light emitting diode, a field effect transistor or a photo-voltaic device.

19. An electronic device according to claim 18, wherein said device is a light emitting diode.

* * * * *